United States Patent [19]
Danielson et al.

[11] Patent Number: 5,993,891
[45] Date of Patent: Nov. 30, 1999

[54] PRUNING SEALANT COMPOSITION AND METHODS OF MAKING AND USING

[75] Inventors: Sheldon G. Danielson, Edina; Donald M. Knutson, Minneapolis, both of Minn.

[73] Assignee: Intagra, Inc., Minneapolis, Minn.

[21] Appl. No.: 09/069,556

[22] Filed: Apr. 29, 1998

[51] Int. Cl.$^6$ .............................. A01G 7/06; A01G 13/00; A01N 3/00
[52] U.S. Cl. .............................. 427/4; 47/58; 47/DIG. 11; 106/15.05; 106/18; 106/18.29
[58] Field of Search .............................. 106/15.05, 18.29, 106/18; 47/58, DIG. 11; 427/4; 514/772, 784, 787

[56] References Cited

U.S. PATENT DOCUMENTS

| | | | |
|---|---|---|---|
| 4,544,666 | 10/1985 | Thirumalachar | 514/460 |
| 5,395,851 | 3/1995 | Sedun | 514/494 |

OTHER PUBLICATIONS

"Tree Wound Dressing," American Nurseryman, vol. 80, pp. 28–29, Oct. 1, 1944.

Bloch, Robert, "Wound Healing in Higher Plants. II.," The Botanical Review, vol. XVIII, No. 10, pp. 655–679, Dec. 1952.

Blanco–Brana, A. et al., "Effects of Applying Growth–Regulating Hormones Following Fruit Tree Pruning. I. Effects of Different Types and Concentrations of Auxin and of GA4+7 and 6–benzylamino Purine on Shoot Emergence and Wound Healing of Apple Trees," Journal of Horticultural Science, vol. 57, No. 1, pp. 17–30, 1982 No Month.

Bose, S.K. et al., "Effect of Various Chemicals and Growth Hormones on Callus Formation on Pruned Surface of Apple Trees," Progressive Horticulture, vol. 10, No. 2, pp. 51–54, Jul.–Sep. 1978.

Crowdy, S.H., "Observations on the Effect of GrowthStimulating Compounds on the Healing of Wounds on Apple Trees," Annals of Applied Biology, vol. 40, pp. 197–207, 1953 No Month.

Davis, Edwin, "Effects of Several Plant Growth–Regulators on Wound Healing of Sugar Maple," Botanical Gazette, vol. 111, pp. 69–77, 1949 No Month.

Davis, Edwin et al., "The Wound Healing of Trees as Affected by Plant Growth Regulating Substances," American Society for Horticultural Science, vol. 53, pp. 233–238, 1949 No Month.

Dessureault, M. et al., "Effect of Growth Substances and Other Compounds on Callus Formation and Discoloration Following Wounding of Red Maples," Phytopathology, vol. 64, Jan.–Dec. 1974.

Neely, Dan, "Wound Closure Rates on Trees," Journal of Aboriculture, vol. 14, No. 10, pp. 250–254, 1988 No Month.

McQuilkin, W.E., "Effects of Some Growth Regulators and Dressings on the Healing of Tree Wounds," Journal of Forestry, vol. 48, pp. 423–428, Sep. 1950.

Neely, Dan, "Tree Wound Closure," Journal of Arboriculture, vol. 14, pp. 148–152, 1988 No Month.

Hunt, R.S., "Evaluation of Wound Dressing on Red Alder," Bimonthly Forestry Notes: Forest Research Centre, Victoria, B.C., p. 19, 1985 No Month.

Perry, E. et al., "Wound Closure in Eucalyptus," Journal of Aboriculture, vol. 13, No. 8, pp. 201–202, Aug. 1987.

Shear, G.M., "Lanolin as a Wound Dressing for Trees," American Society for Horticultural Science., vol. 34, pp. 286–288, 1936 No Month.

Shigo, A.L. et al., "Wound Dressings on Red Maple and American Elm: Effectiveness After Five Years," Journal of Aboriculture, vol. 3, No. 5, pp. 81–87, May 1977.

Tamir, Pinchas, "A Better Dressing for the Treatment of Pruning Wounds," Plant Disease Reporter, vol. 37, No. 4, p. 259, Apr. 15, 1953.

Tilford, Paul E., "Tree Wound Dressings," International Shade Tree Conference, vol. 16, pp. 41–53, 1940 No Month.

Bloch, Robert, "Wound Healing in Higher Plants," The Botanical Review, vol. 7, No. 3, pp. 110–146, Mar. 1941.

Chemical Abstract No. 76:31205, abstract of article by Parups entitled "Use of 6–benzylaminopurine . . . greenhouse roses", HortScience 6(5), 456–7, 1971 No Month.

Chemical Abstract No. 87:79842, abstract of article by Faber et al entitled "The effect of pruning . . . rose plant renewal", J. Am. Soc. Hortic. Sci., 102(2), 223–5, 1977 No Month.

WPIDS Abstract No. 86–154960, abstract of Soviet Union Patent Specification No. 1194347, Nov. 1985.

WPIDS Abstract No. 87–055555, abstract of Soviet Union Patent Specification No. 1242090, Jun. 1986.

WPIDS Abstract No. 90–364030, abstract of Hungarian Patent Specification No. 3485, Oct. 1990.

*Primary Examiner*—Anthony Green
*Attorney, Agent, or Firm*—Michael S. Sherrill

[57] ABSTRACT

A pruning sealant composition comprising lanolin and a drying agent effective for forming a film upon an exposed surface of the pruning sealant composition. An optional high temperature viscosity modifier may be included in the sealer composition. Also disclosed is a method of making the pruning sealant composition and a method of sealing a pruning site with the pruning sealant composition.

20 Claims, No Drawings

PRUNING SEALANT COMPOSITION AND METHODS OF MAKING AND USING

FIELD OF THE INVENTION

The invention relates to a pruning sealant composition, as well as a method of making and using the pruning sealant composition.

BACKGROUND OF THE INVENTION

When a limb or twig of a plant is cut, the plant is injured. The injured plant immediately begins a process of damage containment and repair of the injury. This process includes a collapse of the damaged cells at the cut surface in an effort to reduce "bleeding." Bleeding results in a loss of plant fluids as drying of the exposed surface commences. Drying is not confined to the surface layer of cells at the cut. Often, cells as deep as half an inch within the plant experience fluid loss and drying. A reduction in such drying is generally believed to be beneficial to the healing process by allowing the plant to maintain higher moisture levels at the wound site and prevent such cells from dying. Such cells can then continue to grow and form callus tissue over the surface of the wound.

Various compounds and mixtures have been used on tree and shrub wounds to prevent drying and promote healing. Most are based on paint, shellac or asphalt-derived compounds. These compounds have generally been found to actually retard the healing process.

Lanolin has been recognized for many years as an effective pruning sealant. Lanolin is generally believed to promote healing by preventing drying and die-back, thereby allowing callus to form promptly at the wound edges. However, the viscosity of lanolin at temperatures in excess of about 70° F. is so high that the lanolin tends to drip from a pruning site without forming a protective coating.

An extensive study of wound closure on trees was performed by McQuilkin in the 1940s, with the results published in the *Journal of Forestry* in 1950. Various sealing compositions were tested, including lanolin blended with rosin and/or pine gum. While found to be effective as a pruning sealant, lanolin blended with rosin and/or pine gum is a tacky mass which is difficult to manufacture, handle and apply. The blend also tends to remain tacky for days after application, with the tacky mass attracting and trapping a variety of insects at the application site.

Thus, there is an unmet need for a plant pruning sealant composition which is easy to apply and effective at typical environmental temperatures ranging from 40° to 120° F. for both reducing drying and die-back at a pruning site and preventing insects from accessing the pruning site.

SUMMARY OF THE INVENTION

A pruning sealant composition comprises lanolin and a drying agent effective for forming a film upon an exposed surface of the pruning sealant. An optional high temperature viscosity modifier may be included in the sealant composition.

Also disclosed is a method of making a pruning sealant composition, comprising blending lanolin and a drying agent at elevated temperature to produce a substantially homogeneous blend.

Finally, the invention includes a method of sealing a pruning site comprising: obtaining a composition comprising a blend of lanolin and a drying agent, pruning a plant to form a pruning site, and coating the pruning site with the composition.

DETAILED DESCRIPTION OF THE INVENTION INCLUDING A BEST MODE

Definitions

As utilized herein, including the claims, the term "pruning site" means the area produced by severance of the protective outer layer of a plant, including the removal of a portion of that plant resulting from such actions as mechanical pruning, animal damage, insect damage, storm damage, etc.

As utilized herein, including the claims, the term "drying agent" means any substance which, upon exposure to the atmosphere, forms a surface film which retards the passage of substances, particularly water, through that film.

As utilized therein, including the claims, the term "bactericide" means any substance which kills or retards the growth of bacteria.

As utilized therein, including the claims, the term "fungicide" means any substance which kills or retards the growth of fungus.

As utilized therein, including the claims, the term "pesticide" means any substance which kills or repels animal pests.

As utilized therein, including the claims, the term "insecticide" means any substance which kills or repels insects.

As utilized therein, including the claims, the term "animal repellent" means any substance which repels insects or animal pests.

As utilized herein, including the claims, the term "wt %" means the percentage by weight of the constituents in a mixture.

Composition

The pruning sealant composition comprises lanolin, a drying agent and optionally a high temperature viscosity modifier. The pruning sealant composition can further include one or more specialty agents selected from a bactericide, a fungicide, a pesticide, an insecticide, and an animal repellent. The preferred blend of lanolin, "drying" vegetable oils, and bees wax is a nearly odorless, slightly tan composition that is easy to handle and apply to a pruning site.

LANOLIN

The lanolin used is preferably a USP technical grade of lanolin, although various other grades, including the least refined "wool-grease," are acceptable.

The pruning sealant composition preferably includes about 30 to 70 wt % lanolin.

DRYING AGENT

Lanolin is an excellent moisturizer, containing up to about 25 wt % water. When exposed to the environment the water within the lanolin will evaporate, thereby reducing the moisturizing capacity of the lanolin and eventually rendering the lanolin ineffective as a moisturizer. The present invention extends the moisturizing effect of lanolin by incorporating a drying agent into the lanolin. The drying agent is effective for forming a film upon the exposed surface of the pruning sealant composition once the composition is coated onto a pruning site. Without intending to be limited to any theory, it is believed that the drying agent migrates to the exposed surface of the coating and is oxidized by oxygen in the atmosphere to form a dry, nontacky, moisture impermeable film on the exposed surface of the coating. The film, by reducing evaporation from the underlying layer of lanolin, maintains the moisturizing effect of the lanolin for an extended period of time. The film also serves to holds the lanolin in position over a pruning site at elevated temperatures, effectively functioning as a structural barrier surrounding the lanolin and preventing the lanolin from flowing away from the pruning site.

The drying agent should be fully compatible with the other constituents in the pruning sealant composition, and preferably does not significantly reduce the viscosity of the composition. Suitable drying agents include, but are not limited to, "drying" vegetable oils. Preferred "drying" vegetable oils include refined linseed oil, boiled linseed oil, tung oil, and mixtures of these three oils. Linseed oil is frequently modified to achieve different performance characteristics with respect to drying. The linseed oil resulting from such modifications, listed in order from the slowest drying type to the fastest drying type, are raw, refined, bleached, defatted, sun thickened, aged or blown, boiled, and double boiled.

In a preferred embodiment of the invention, the drying agent is a blend of refined linseed oil, boiled linseed oil and tung oil. Each of these oils is commercially available from numerous suppliers.

In a most preferred embodiment of the invention, the drying agent comprises a mixture of boiled linseed oil and tung oil. This composition provides a strong, flexible surface film that forms quickly upon application of the pruning sealant composition to a pruning site.

The pruning sealant composition preferably includes about 20 to 55 wt % drying agent.

SOFTENING AGENT

Vegetable oils capable of contributing a "softening" effect upon the composition may be incorporated into the composition along with the drying agent. Soft vegetable oils include soy, canola, corn, cotton and other seed oils. The soft oils are not noted for their drying qualities, but are rather used to enhance spreadability of the composition over extended storage periods without significantly impeding formation of a surface film once the composition is applied to a pruning site.

Raw linseed oil and refined linseed oil, while recognized as a drying agent, also contribute soft oil characteristics to the composition.

HIGH TEMPERATURE VISCOSITY MODIFIER

Lanolin melts at 110° F. and tends to flow under the force of gravity at temperatures in excess of 70° F. Thus, lanolin alone is generally ineffective as a pruning sealant because it does not remain on the pruning site for a sufficient period of time when ambient temperatures are above about 70° F.

A high temperature viscosity modifier can be added to the pruning sealant composition for purposes of increasing the viscosity of the composition at those environmentally encountered temperatures where lanolin tends to flow under the force of gravity (i.e., temperatures between about 70° F. and 110° F.). The high temperature viscosity modifier may be selected from a number of known high temperature viscosity modifiers, such as resins, rosins, propylis, tars, or pine gum. Preferred high temperature viscosity modifiers are those which are compatible with the other constituents and do not render the composition tacky. A particularly suitable high temperature viscosity modifier is bees wax.

The pruning sealant composition preferably includes about 10 to 30 wt % high temperature viscosity modifier.

SPECIALTY AGENTS

The pruning sealant composition can include a specialty agent selected from the group consisting of a bactericide, a fungicide, a pesticide, an insecticide, and an animal repellent. Specific examples of such specialty additives include (i) anti-bacterial and antifungal agents, such as streptomycin sulfate, benlate and various copper based compounds, (ii) insect repellents and insect anti-feedants such as Neem oil, DEET, and citronella, and (iii) animal repellents and anti-feedants such as putrescent egg materials, capsaicin, oil of garlic and oil of mustard.

ADDITIVES

The pruning sealant composition may further include various additives such as (i) plant growth regulators and other biochemical reagents capable of stimulating, retarding, regulating or otherwise affecting plant growth and development, including indole acetic acid or indole butyric acid, (ii) pheromones, (iii) fragrances, and (iv) pigments, dyes and/or colorants.

Process for Making Pruning Sealant Composition

A method of making the pruning sealant composition comprises blending the lanolin and drying agent under conditions of elevated temperature to produce a substantially homogeneous blend. The optional softening agent, high temperature viscosity modifier, specialty agent and/or additive may be added to the blend at the same time (i.e., under conditions of elevated temperature) or while the blend is cooling, dependent upon the thermal sensitivity of the material.

The resultant substantially homogeneous blend may be cast directly into a container and sealed for subsequent storage, transportation and use. Suitable dispensing containers include specifically, but not exclusively, standard screw top wide mouth jars and standard push-up tubes with a friction fitted cover, both containers being well known in the industry.

The pruning sealant composition should be protected from extended exposure to air in order to maintain the integrity of the drying agent. The container may be sealed by any of the well known sealing techniques, such as thermal bonding of a mylar film over the opening. Once the pruning sealant composition is applied to a pruning site, the drying agent begins to form a film over the exposed surface of the coating.

Method of Using

Use of the pruning sealant composition is quick, clean and easy. No special application tools are required and no special solvents or cleansers need be used to clean-up afterwards. Once a pruning site is found or formed, the pruning sealant composition can be coated onto the pruning site directly from the container (ála application of lipstick), by hand (ála application of face creams) or with the aid of an applicator (e.g. a popsicle stick).

The pruning sealant composition should be coated over a pruning site at a coating thickness of between approximately 0.05 cm to 0.5 cm and the surface of the coating allowed to dry.

The pruning sealant composition is suitable for sealing pruning sites on most types of plants. As a premium pruning sealant composition, the composition finds a particularly useful application in the sealing of pruning sites on valuable plants known to be susceptible to damage when pruned, such as rose bushes.

The pruning sealant composition is also suitable for use as a grafting wax.

EXAMPLES

Into a suitable vessel was placed 1 lb. raw linseed oil, 1 lb. boiled linseed oil and 1 lb. tung oil. The oil mixture was heated to 150° F. Into the heated oil mixture was added 2 lbs. of bees wax. The bees wax containing mixture was stirred constantly until the bees wax was fully dissolved. Heating of the bees wax containing mixture was discontinued and 5 lbs. of lanolin added to the mixture. The lanolin containing mixture stirred constantly until the lanolin was homogeneously blended into the mixture and the temperature of the mixture reached about 130° F. The resulting lanolin containing mixture was cast into suitable point-of-use containers and the containers sealed.

We claim:

1. A pruning sealant composition, comprising:
   (a) about 30 to 70 wt % lanolin, and
   (b) about 20 to 55 wt % drying agent effective for forming a film upon an exposed surface of the pruning sealant composition.

2. The composition of claim 1 further comprising about 10 to 30 wt % high temperature viscosity modifier.

3. The composition of claim 1 further comprising an effective amount of an additive selected from the group consisting of a bactericide, a fungicide, an insecticide, an insect repellent and a pesticide.

4. The pruning sealant composition of claim 1 wherein the drying agent is a vegetable oil.

5. The pruning sealant composition of claim 4 wherein the vegetable oil is a blend of refined linseed oil, boiled linseed oil and tung oil.

6. The pruning sealant composition of claim 2 wherein the high temperature viscosity modifier is a wax.

7. A method of making a pruning sealant composition, comprising blending about 30 to 70 wt % lanolin and about 20 to 55 wt % drying agent under conditions of elevated temperature to produce a substantially homogeneous blend.

8. The method of claim 7 further comprising blending about 10 to 30 wt % high temperature viscosity modifier along with the lanolin and drying agent under conditions of elevated temperature to produce a substantially homogeneous blend.

9. The method of claim 7 wherein blending lanolin and a drying agent under conditions of elevated temperature comprises blending lanolin and a vegetable oil under conditions of elevated temperature.

10. The method of claim 9 wherein blending lanolin and a vegetable oil under conditions of elevated temperature comprises blending lanolin and a blend of refined linseed oil, boiled linseed oil and tung oil under conditions of elevated temperature.

11. The method of claim 8 wherein blending lanolin, a drying agent and a high temperature viscosity modifier under conditions of elevated temperature comprises blending lanolin, a drying agent and bees wax under conditions of elevated temperature.

12. The method of claim 7 further comprising casting the blend into a container.

13. The method of claim 12 further comprising sealing the container.

14. A method of sealing a pruning site, comprising:
   (a) obtaining a composition comprising a blend of about 30 to 70 wt % lanolin and about 20 to 55 wt % drying agent,
   (b) pruning a plant to form a pruning site, and
   (c) coating the pruning site with the composition.

15. The method of claim 14 wherein obtaining a composition comprises obtaining a composition comprising about 30 to 70 wt % lanolin, about 20 to 55 wt % drying agent and about 10 to 30 wt % high temperature viscosity modifier.

16. The method of claim 14 wherein obtaining a composition comprising lanolin, a drying agent and a high temperature viscosity modifier comprises obtaining a composition comprising lanolin, a drying agent vegetable oil and a high temperature viscosity modifier.

17. The method of claim 16 wherein obtaining a composition comprising lanolin, a drying agent vegetable oil and a high temperature viscosity modifier comprises obtaining a composition comprising lanolin, a blend of refined linseed oil, boiled linseed oil and tung oil, and a high temperature viscosity modifier.

18. The method of claim 15 wherein obtaining a composition comprising lanolin, a drying agent and a high temperature viscosity modifier comprises obtaining a composition comprising lanolin, a drying agent and bees wax.

19. The method of claim 14 wherein coating the pruning site with the composition comprises coating the pruning site with an approximately 0.05 cm to 0.5 cm thick coating of the composition; and the method further comprises allowing the coated composition to dry.

20. The method of claim 14 wherein pruning a plant to form a pruning site comprises pruning a rose to form a pruning site.

\* \* \* \* \*